(12) United States Patent
Bhaganagar et al.

(10) Patent No.: US 10,983,247 B2
(45) Date of Patent: Apr. 20, 2021

(54) SYSTEMS AND METHODS FOR MEASURING ENVIRONMENTAL PARAMETERS

(71) Applicants: Kiran Bhaganagar, San Antonio, TX (US); Prasanna R V Kolar, San Antonio, TX (US); Sudheer Reddy Bhimireddy, San Antonio, TX (US); Jordan Nielson, San Antonio, TX (US)

(72) Inventors: Kiran Bhaganagar, San Antonio, TX (US); Prasanna R V Kolar, San Antonio, TX (US); Sudheer Reddy Bhimireddy, San Antonio, TX (US); Jordan Nielson, San Antonio, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 16/787,421

(22) Filed: Feb. 11, 2020

(65) Prior Publication Data
US 2020/0257018 A1 Aug. 13, 2020

Related U.S. Application Data

(60) Provisional application No. 62/803,668, filed on Feb. 11, 2019.

(51) Int. Cl.
*G01W 1/04* (2006.01)
*G01N 33/00* (2006.01)
(Continued)

(52) U.S. Cl.
CPC ............... *G01W 1/04* (2013.01); *G01K 13/00* (2013.01); *G01N 25/18* (2013.01);
(Continued)

(58) Field of Classification Search
CPC ......... G01W 1/04; G01K 13/00; G01N 25/18; G01N 33/0075; G01P 13/0006
(Continued)

(56) References Cited

U.S. PATENT DOCUMENTS

| 2005/0051669 | A1* | 3/2005 | Heller | A01C 21/00 244/136 |
| 2012/0232798 | A1* | 9/2012 | Savage | G01W 1/00 702/3 |

(Continued)

FOREIGN PATENT DOCUMENTS

| CN | 104459830 A | * | 3/2015 |
| CN | 105119959 A | * | 12/2015 |

(Continued)

OTHER PUBLICATIONS

English translation of CN107607450 from espacenet.com. accessed Jun. 2, 2020.*

(Continued)

*Primary Examiner* — Nimeshkumar D Patel
*Assistant Examiner* — Jean F Morello
(74) *Attorney, Agent, or Firm* — Thomas | Horstemeyer, LLP

(57) ABSTRACT

The present disclosure describes various systems and methods for measuring environmental parameters. In one embodiment, such as system comprises a pole that is equipped with various instruments (sensors) at various heights along the length of the pole. With such an instrumented pole, a local vertical profile of parameters that relate to wind conditions and air quality can be obtained. These parameters can include one or more of wind speed and direction, air turbulence, air temperature and humidity, concentrations of pollutant gases within the air, and concentrations of pollutant particles within the air. In some embodi- (Continued)

ments, the system can further measure other parameters that are relevant to the migration of the air and, therefore, the pollutants it contains.

20 Claims, 2 Drawing Sheets

(51) Int. Cl.
  *G01K 13/00* (2021.01)
  *G01W 1/14* (2006.01)
  *G01N 25/18* (2006.01)
  *G01P 13/00* (2006.01)
(52) U.S. Cl.
  CPC ...... *G01N 33/0075* (2013.01); *G01P 13/0006* (2013.01); *G01W 1/14* (2013.01)
(58) Field of Classification Search
  USPC .......................................................... 73/29.01
  See application file for complete search history.

(56) References Cited

U.S. PATENT DOCUMENTS

2016/0273879 A1\* 9/2016 Volfson .................... G01W 1/02
2020/0278475 A1\* 9/2020 Shao ........................ G01S 7/497

FOREIGN PATENT DOCUMENTS

CN     105717068 A  \*  6/2016
CN     107607450 A  \*  1/2018

OTHER PUBLICATIONS

English translation of CN105119959 from espacenet.com. accessed Jun. 2, 2020.\*
English translation of CN10459830 from espacenet.com. accessed Jun. 2, 2020.\*
English translation of specification for CN105717068 accessed from espacenet.com.\*

\* cited by examiner

SYSTEMS AND METHODS FOR MEASURING ENVIRONMENTAL PARAMETERS

CROSS-REFERENCE TO RELATED APPLICATION

This application claims priority to U.S. provisional application entitled, "Systems and Methods for Measuring Environmental Parameters," having Ser. No. 62/803,668, filed Feb. 11, 2019, which is entirely incorporated herein by reference.

NOTICE OF GOVERNMENT-SPONSORED RESEARCH

This invention was made with Government support under grant contract number DO1_W911SR-14-2-0001-0006 awarded by the U.S. Army Edgewood Chemical Biological Center (ECBC). The Government has certain rights in the invention.

BACKGROUND

It is important to measure and track local values of air quality and wind conditions as pollutants within the air can cause allergies, diseases, and even death to humans. In addition, airborne pollutants can cause harm to other living organisms, including animals, plants, and food crops.

Currently, air quality and wind conditions are typically monitored using meteorological towers. While such towers are effective in collecting certain desired parameters, they are extremely expensive and stationary. Because they are stationary, they can only provide information about the local wind conditions and air quality in the vicinity of the tower. Simple, handheld devices are also available, which are much less expensive and portable. While such devices provide greater convenience, they are often inaccurate and, therefore, of relatively little benefit.

Needed are systems and methods that can be used to measure environmental parameters relevant to air quality and local wind conditions that are inexpensive, accurate, mobile, and that can be accessed remotely. If such systems and methods existed, the relevant environmental parameters could be acquired at multiple locations around a given area, such as a city or other population center, so as to provide a highly accurate indication as to important information that affects humans, animals, and the environment.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, needed are inexpensive, accurate, and mobile systems and methods that can be used to measure environmental parameters relevant to air quality and wind conditions. Disclosed herein are examples of such systems and methods. In some embodiments, a system for measuring environmental parameters comprises a pole that is equipped with various instruments (sensors) at various heights along the length of the pole. With such an instrumented pole, a local vertical profile of parameters that relate to wind conditions and air quality can be obtained. These parameters can include one or more of wind speed and direction, air turbulence, air temperature and humidity, concentrations of pollutant gases within the air, and concentrations of pollutant particles within the air. In some embodiments, the system can further measure other parameters that are relevant to the migration of the air and, therefore, the pollutants it contains. For example, the system can include surface flux sensors that measure the direction of heat transfer along the ground, which creates microturbulence that affects the direction in which the air travels. When multiple systems of the like described above are deployed in a given region, a highly accurate picture of the atmospheric pollution conditions in the region can be obtained.

In the following disclosure, various specific embodiments are described. It is to be understood that those embodiments are example implementations of the disclosed inventions and that alternative embodiments are possible. Such alternative embodiments include hybrid embodiments that include features from different disclosed embodiments. All such embodiments are intended to fall within the scope of this disclosure.

Figure 1:
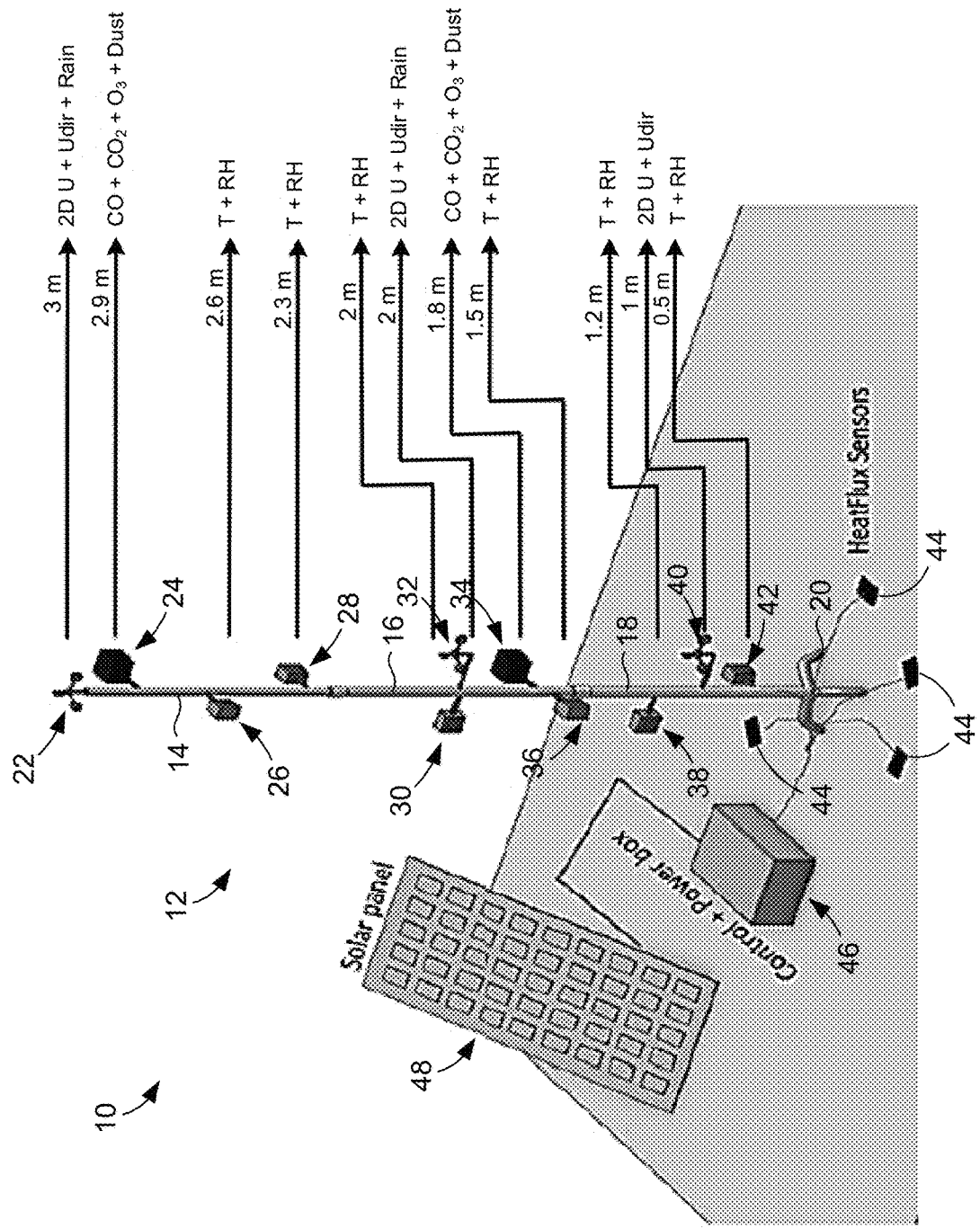
FIG. 1 is a schematic view of an embodiment of a system for measuring environmental parameters.

FIG. 1 illustrates an example embodiment of a system 10 for measuring environmental parameters. As shown in this figure, the system 10 includes an elongated pole 12 upon which various instruments are mounted for the purpose of measuring parameters that are relevant to air composition and migration. In some embodiments, the pole 12 is modular and comprises multiple pole segments 14, 16, and 18 that connect to each other end-to-end to create the full-length pole.

Each pole segment 14-18 can comprise a hollow tube or pipe that is made out of a rigid material, such as a metal or a polymer material. In addition, each pole segment 14-18 can comprise a connector at one or both ends that is adapted to mate with a connector of an adjacent pole segment. For example, the mating ends of the pole segments 14-18 can simply have different outer diameters to facilitate one end fitting within another end. In the illustrated embodiment, the pole 12 comprises three equal-length pole segments 14-18, which are each approximately 1 m long. In addition to the pole segments 14-18, the pole 12 includes a tripod base 20 that can be staked to the ground. The base 20 enables the pole 12 to stand upright without falling over in the wind. In the illustrated embodiment, the pole 12 is approximately 3 m tall when fully assembled and weighs only approximately 7.5 kg such that the pole 12 can be easily transported. With the 3 m height, air parameters can be collected within the lower portion of the atmospheric boundary layer of air that passes over the earth's surface. Computer modeling performed by the inventors has revealed that collecting data within this portion of the boundary layer is sufficient to obtain an accurate profile of air composition and migration.

As shown in FIG. 1, the pole segments 14-18 and, therefore, the pole 12, support various instruments that measure air parameters. Beginning with the top pole segment 14, mounted at a height of approximately 3 m is a first weather meter 22 that includes a cup-type anemometer for measuring wind speed, a wind vane for measuring wind direction, and a rain gauge. By way of example, the weather meter 22 can comprise a Sparkfun SEN08942 weather meter.

At a height of approximately 2.9 m is an open-bottomed enclosure 24 that contains pollution sensors, which include multiple gas sensors and a particulate sensor. These sensors can comprise a carbon monoxide (CO) sensor, a carbon dioxide ($CO_2$) sensor, an ozone ($O_3$) sensor, and a particulate sensor. By way of example, the CO sensor can be a Grove MQ3 semiconductor-based gas sensor that is capable of measuring up to 500 ppm of CO gas, the $CO_2$ sensor can be a Sensiron SCD30 nondispersive infrared (NDIR)-based sensor that is capable of measuring up to 400-10,000 ppm of $CO_2$ gas, the $O_3$ sensor can be a Grove MQ131 semiconductor-based gas sensor that is capable of measuring up to 2 ppm of $O_3$ gas, and the particulate sensor can be a Grove PPD42NS dust sensor that is capable of detecting particles of sizes $1 \times 10^{-3}$ mm and greater. Each of the sensors within the enclosure 24 is shielded from the elements (e.g., rain and snow) but is still exposed to the ambient air so that accurate readings can be obtained.

At heights of approximately 2.6 m and 2.3 m are two further open-bottomed enclosures 26 and 28 that each contains a temperature sensor and a relative humidity sensor. As above, these sensors are shielded from the elements by their respective enclosures 26, 28 but are still exposed to the ambient air so that accurate readings can be obtained.

Turning to the middle pole segment 16, at a height of approximately 2 m is a further enclosure 30 that contains a temperature sensor and a relative humidity sensor as well as a second weather meter 32 having a construction similar to that of the first weather meter 22.

At a height of approximately 1.8 m is a further open-bottomed enclosure 34 that also contains a CO sensor, a $CO_2$ sensor, an $O_3$ sensor, and a particulate sensor. These sensors can be the same as those described above in relation to the enclosure 24.

At a height of approximately 1.5 m is a further enclosure 36 that contains a temperature sensor and a relative humidity sensor.

Finally, turning to the bottom pole segment 18, at a height of approximately 1.2 m is a further open-bottomed enclosure 38 that contains a temperature sensor and a relative humidity sensor. At a height of approximately 1 m is a third weather meter 40 having a construction similar to that of the first and second weather meters 22 and 34. At a height of approximately 0.5 m is yet another open-bottomed enclosure 42 that contains a temperature sensor and a relative humidity sensor.

Table 1 below provides a summary of the above-noted measured parameters and the heights at which they are measured.

TABLE 1

Measured Parameters and Heights of Measurements

| Notation | Atmospheric Variable | Measured height |
| --- | --- | --- |
| U | Wind speed | ground, 1 m, 2 m, and 3 m above the ground |
| UDir | Wind Direction | ground, 1 m, 2 m, and 3 m above the ground |
| RH | Relative humidity | 0.5 m, 1.2 m, 1.5 m, 1.8 m, 2 m, 2.3 m, 2.6 m and 2.9 m above the ground |
| T | Temperature | 0.5 m, 1.2 m, 1.5 m, 1.8 m, 2 m, 2.3 m, 2.6 m and 2.9 m above the ground |
| CO | Carbon monoxide | 1.8 m and 2.9 m above the ground |
| $CO_2$ | Carbon Dioxide | 1.8 m and 2.9 m above the ground |
| $O_3$ | Ozone | 1.8 m and 2.9 m above the ground |
| Dust | Dust | 1.8 m and 2.9 m above the ground |
| HeatFlux | Surface heat flux | On the ground using 4 sensors |
| Turbulence | Wind velocity fluctuations | 3 m above the ground |

Notably, the height at which each air parameter is measured is not arbitrary. To the contrary, the various heights were determined by the inventors through computer modeling to identify the parameters and heights that are most useful in obtaining a full and accurate profile of air composition and migration.

In addition to the above-described air parameters, other relevant environmental parameters can be measured. For example, surface heat flux can be measured at various locations on the ground with multiple surface heat flux sensors 44. In the illustrated embodiment, four heat flux sensors 44 are provided. By way of example, the heat flux sensors 44 can be FluxTeq PHFS-09e heat flux sensors, which are approximately 0.6 mm thick and cover an 88 mm×95 mm area to measure heat flux within +/−150 $kWm^{-2}$. The heat flux sensors 44 can, for instance, be placed at spaced locations that are approximately 0.03 m from the base 20 of the pole 12.

Each of the sensors described above is connected to a control module 46 with electrical cables. For the sensors mounted to the pole 12, the cables can be routed through the hollow interior space of the various pole segments 14-18. While cables are depicted in FIG. 1 and have been explicitly identified, it will be appreciated that one or more of the sensors could be wirelessly connected to the control-power module 46 if configured for such wireless communication. As is further shown in FIG. 1, the system 10 also includes a power source in the form of a solar panel 48 that is also connected to the control module 46. When provided, the solar panel 48 can generate power for the system 10 from absorbed sunshine.

Figure 2:
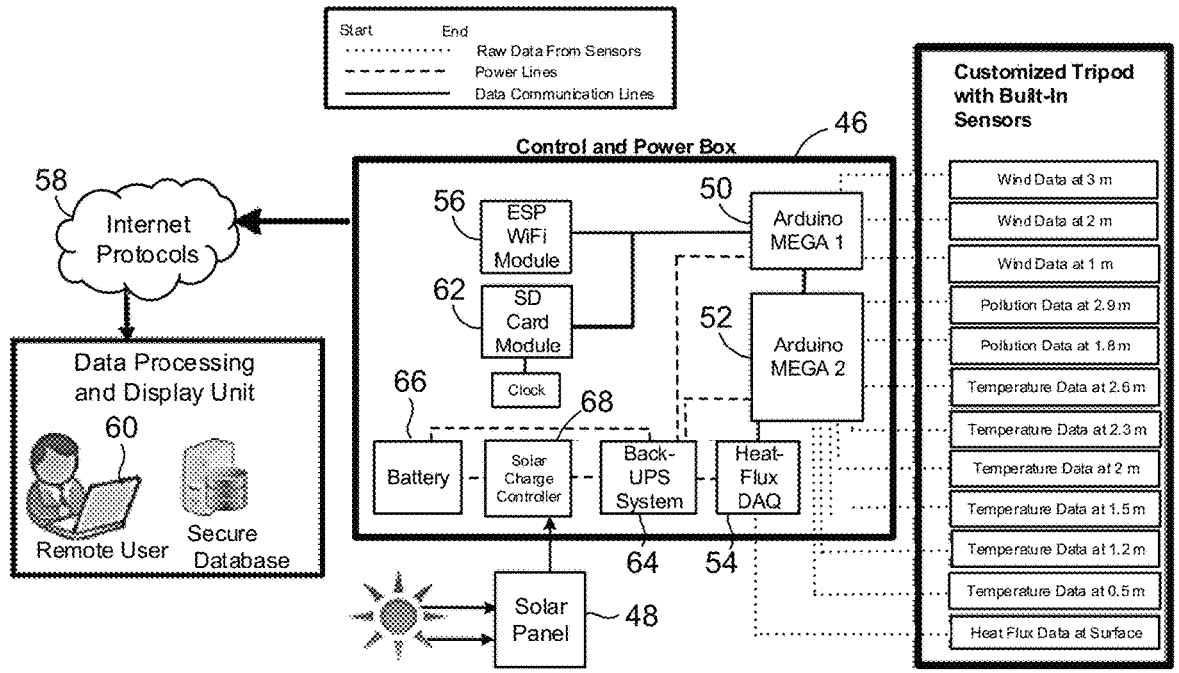
FIG. 2 is a block diagram of an embodiment of a control module shown in FIG. 1.

FIG. 2 illustrates an example architecture for the control module 46 and further illustrates the communication of data to the module from the various sensors as well as communication from the module to a remote location via a network. As shown in the figure, the control module 46 can include two microcontrollers 50 and 52 (e.g., Arduino microcontrollers) that receive data from the sensors mounted to the pole 12, and a heat flux data acquisition unit 54 that receives data from the surface heat flux sensors 44. In the illustrated embodiment, the first microcontroller 50 collects the data from the weather meters, while the second microcontroller 52 collects the data from temperature, humidity, and pollution sensors. The output from the surface heat flux sensors 44 is on the order of millivolts and cannot be captured by a standard Arduino microcontroller, so the data acquisition unit 54 is used to collect the heat flux data. In some embodiments, the output frequency of the pollution, temperature, and humidity sensors is approximately 2 seconds, while the output frequency for weather meters and surface heat flux sensors is approximately 1 second.

The first microcontroller 50 collects all the measured data after communicating with the second microcontroller 52, which collects data from the data acquisition unit 54. All of this data is then sent to a web-based client, via a wireless (e.g., WiFi) module 56 (e.g., ESP8266 NodeMCU microcontroller module) and a wireless network 58, where the data can be received at a remote computer 60 and viewed nearly in real time. In addition to this, the raw data can also be stored locally in a text file on an SD card within an SD card module 62 for post-processing purposes. For consistency, the data transmitted to the remote computer 60 is updated every 2 seconds, while the data stored on the SD card is stored at the individual sensors' frequency. This can be achieved by writing the weather meter data to a single file and rest of the sensors' data to a second file on the SD card.

As noted above, the system 10 can be powered using the solar panel 48. In some embodiments, the solar panel 48 can comprise a 100 W solar panel that is mounted on a manually adjustable 1-axis tilt stand. In some embodiments, power to the microcontrollers 50, 52 and the data acquisition unit 54 is supplied from a backup and surge protector 64, such as the 330 W Back-UPS system, which is connected to a backup battery 66, such as a 12 V 35 Ah battery. The solar panel 48 is connected to the backup battery 66 via a solar charge controller 68 that controls the flow of power among the battery and backup and surge protector 64. Input power to the sensors can be maintained at a constant 5.1 V by a dedicated DC-to-DC step-down converter that is connected to the backup and surge protector 64.

In some embodiments, data collection begins when the control module 46 is powered. Once an initialization is completed, a control program stored in one of the microcontrollers 50, 52 detects the available wireless networks and uses the network credentials given by a user to connect to the specified network 58. Once a connection is established, the control program checks for the SD card to save the sensor data. If an SD card is detected, the program begins logging the data in a new file each new day at midnight. This way, each day's data will be stored in a single file. Once a file is created, the control program collects and logs the sensor data.

Figure 3:
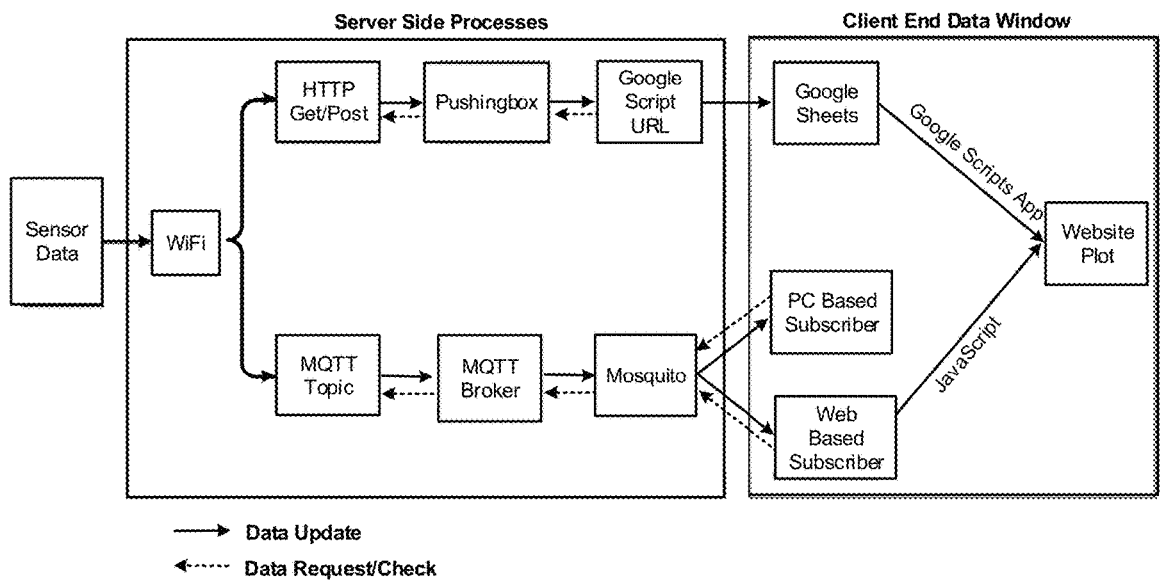
FIG. 3 is a block diagram of an embodiment of a communication protocol that can be used to transmit data collected by the system of FIG. 1.

In some embodiments, NodeMCU is used to publish sensor data to the cloud. NodeMCU is an IoT platform running on ESP8266 firmware that can connect to wireless networks. The usual communication of data over the internet occurs between a web server and a single or multiple clients. A web server is the node that publishes the sensor data via the internet, and the client is the node that receives the data. Two different protocols have been developed to establish communication from a server to the client, including hypertext transfer protocol (HTTP) and message queuing telemetry transport (MQTT). For the former, data can be written to Google Sheets using HTTP, and, for the latter, data can be written to a cloud service using MQTT (see FIG. 3).

In order to publish sensor data to Google Sheets, a cloud notification service known as PushingBox can be used. PushingBox has a simple architecture in which it has only one application program interface (API) that can be triggered by sending a simple HTTP command. The Google Sheets service creates a unique API key for each workbook created in it. Using this API key and PushingBox GET/POST commands, a simple HTTP request/response can be written into the control program to send data. On the receiving end, Google Sheets runs a Google app script that receives the data from PushingBox and pastes it in a user-specified Google Sheet. The only limitation of this method is that PushingBox handles 1,000 API requests a day. Data from all the sensors can be sent out in a single API request, so the total requests made in a day depends on the frequency at which the Google Sheet is to be updated. For example, if data is written to Google Sheets every minute, then one would require to activate/trigger the PushingBox HTTP command a total of 1,440 times, which exceeds the current limitation. So, data can be written to Google Sheets every 90 seconds, which uses a total of 960 API requests.

HTTP requires time to communicate but is helpful to check/monitor the whole system health. For sending data at higher frequencies, MQTT can be used. MQTT requires a "broker" application that collects and transfers data between clients. Data from sensors can be sent/published to a "topic" created with the MQTT protocol. The MQTT broker is configured to listen to this topic and send/distribute the published data to all the clients who subscribe to the topic thread. This can provide an advantage over HTTP, in which multiple POST commands are to be executed for sending the data to multiple clients. Multiple open-source MQTT broker applications are available. Mosquito is one such broker that can be accessed through command-line utilities for publishing or subscribing to topics. Once the MQTT broker begins collecting data for a topic, the receiving client can be on any platform, such as a computer or a web-based application. On a generic computer or a local server, the web-based programing tool Node-Red can be used to subscribe to the MQTT topics and read the data. Once the data is read, it can be stored on a database or sent to a live chart application where the user can see real-time graph of the data values.

After the data has been collected at the client end, the data can further flow on to a web-based plot through a third-party application. In the case of data published on to Google Sheets, a Google app scripting tool can be used to create a JavaScript object notation (JSON) object with the data and push it to a custom website. In the case of data published via the MQTT protocol, a web-based subscriber can use the data being collected to create a plot for visualizing the data via JavaScript.

When the above-disclosed system is operated, it can determine the atmospheric stability, microturbulence, and pollution levels at a given location in real time. Data-processing algorithms can then be used to evaluate atmospheric stability and wind/pollutant vertical profiles, and to visually display the pollution and microturbulence.

In summary, the disclosed system can be used to: Detect pollution levels ($CO$, $CO_2$, $O_3$, and particulate matter) in real time; Determine microturbulence levels in the atmospheric boundary layer; Determine vertical wind speed profiles, wind direction, and air temperature profiles; Determine surface temperature and surface heat flux; and Detect chemical plumes in the atmosphere. The features of the disclosed system include Full microturbulence, wind, weather conditions, and chemical monitoring at 2 Hz frequency; Portability; No external power source required; Atmospheric data-processing and web-based visual display; and Remote access from any computer with internet connectivity. Applications for the disclosed system include: Residential communities, schools, and public offices; Environmental applications; Wind farms; Utilities; Agricultural applications; Homeland security; Public places such as sports venues; and Air-quality regulatory applications.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure.

The invention claimed is:

1. A system for measuring environmental parameters, the system comprising:
an elongated pole having at least three vertical sections; and
multiple sensors mounted to the elongated pole at predetermined locations relative to a ground and configured to measure the environmental parameters along a local vertical profile of the elongated pole, wherein the environmental parameters include air temperature parameters, humidity parameters, wind speed parameters, wind direction parameters, gas parameters, and particulate matter parameters, wherein the multiple sensors include:
air temperature and humidity sensors mounted to the elongated pole at different vertical locations within each of the three vertical sections;
wind speed and direction sensors mounted to the elongated pole at each of the three vertical sections; and
pollution sensors mounted to the elongated pole within at least two of the three vertical sections, the pollution sensors configured to measure carbon monoxide, carbon dioxide, ozone, and particulate matter within the local vertical profile.

2. The system of claim 1, wherein the elongated pole is comprised of multiple pole segments that connect together.

3. The system of claim 2, wherein the multiple sensors are mounted to each pole segment at predetermined locations.

4. The system of claim 3, wherein the elongated pole is approximately 3 meters tall.

5. The system of claim 4, wherein the elongated pole comprises 3 pole segments, each pole segment approximately 1 meter long.

6. The system of claim 1, wherein the multiple sensors further include sensors configured to measure rainfall.

7. The system of claim 1, further comprising heat flux sensors that are configured to be placed on the ground adjacent the elongated pole.

8. The system of claim 1, further comprising a control module configured to receive data collected by the sensors.

9. The system of claim 8, wherein the control module is further configured to wirelessly transmit the received data to a remote computer.

10. The system of claim 8, further comprising a power source that powers the sensors and the control module.

11. The system of claim 10, wherein the power source comprises a solar panel.

12. The system of claim 9, wherein the remote computer is configured to detecting a chemical plume in the atmosphere by determining wind and pollutant vertical profiles at the elongated pole based on the measured environmental parameters.

13. The system of claim 1, further comprising: heat flux sensors that are configured to be placed on the ground adjacent the elongated pole; a control module configured to receive data collected by the sensors and wirelessly transmit the received data to a remote computer; and the remote computer configured to detect a chemical plume in the atmosphere by determining wind and pollutant vertical profiles at the elongated pole based on the measured environmental parameters and a measure of heat transfer along the ground from the heat flux sensors.

14. A method for measuring environmental parameters, comprising:
mounting multiple sensors that are configured to measure the environmental parameters to an elongated pole;
wherein the sensors are mounted at predetermined locations relative to a ground along a local vertical profile of the elongated pole, wherein the environmental parameters include air temperature parameters, humidity parameters, wind speed parameters, wind direction parameters, gas parameters, and particulate matter parameters, wherein the multiple sensors include:
air temperature and humidity sensors mounted to the elongated pole at different vertical locations within each of three vertical sections of the elongated pole;
wind speed and direction sensors mounted to the elongated pole at each of the three vertical sections; and
pollution sensors mounted to the elongated pole within at least two of the three vertical sections, the pollution sensors configured to measure carbon monoxide, carbon dioxide, ozone, and particulate matter within the local vertical profile;
positioning the elongated pole at various locations on a ground;
measuring parameters relevant to air composition and air migration within the local vertical profile from the multiple sensors; and
detecting a chemical plume in the atmosphere by determining, via a computing device, wind and pollutant vertical profiles at the elongated pole based on at least the measured parameters.

15. The method of claim 14, wherein a height of the elongated pole is approximately 3 meters tall.

16. The method of claim 14, wherein the elongated pole comprises a top pole section, a middle pole section, and a lower pole section, wherein first pollution sensors, a first weather meter sensor, a first temperature sensor, and a first humidity sensor are mounted within the top pole section; second pollution sensors, a second weather meter sensor, a second temperature sensor, and a second humidity sensor are mounted within the middle pole section, and a third weather meter sensor, a third temperature sensor, and a third humidity sensor are mounted in the top pole section.

17. The method of claim 14, further comprising powering the multiple sensors from a solar panel that is mounted to the elongated pole.

18. The method of claim 17, wherein no external power source is utilized to power the multiple sensors, collect data from the multiple sensors, or transmit the data to a remote computer.

19. The method of claim 14, further comprising collecting data from the multiple sensors and wirelessly transmitting the data to a remote computer.

20. The method of claim 14, further comprising: positioning heat flux sensors on the ground adjacent the elongated pole, wherein the chemical plume is detected based on the measured parameters and a measure of heat transfer along the ground from the heat flux sensors.

* * * * *